United States Patent [19]

Yamaguchi et al.

[11] Patent Number: 4,501,278
[45] Date of Patent: Feb. 26, 1985

[54] ULTRASONIC PROBE FOR PUNCTURE TREATMENT

[75] Inventors: Keiki Yamaguchi; Shinichi Sano, both of Tokyo, Japan

[73] Assignee: Yokogawa Hokushin Electric Corporation, Tokyo, Japan

[21] Appl. No.: 555,356

[22] Filed: Nov. 28, 1983

Related U.S. Application Data

[63] Continuation of Ser. No. 344,361, Feb. 1, 1982, abandoned.

[30] Foreign Application Priority Data

Feb. 9, 1981 [JP] Japan .................................. 56-16942

[51] Int. Cl.³ .............................................. A61B 5/00
[52] U.S. Cl. ..................................... 128/660; 128/653; 73/629
[58] Field of Search ................. 128/660–663, 128/653, 657, 751, 754, 654; 73/620, 622, 627, 629

[56] References Cited

U.S. PATENT DOCUMENTS

| | | | |
|---|---|---|---|
| 3,661,146 | 5/1972 | Peronneau et al. | 128/663 |
| 3,974,692 | 8/1976 | Hassler | 128/663 X |
| 4,058,114 | 11/1977 | Soldner | 128/754 X |
| 4,127,842 | 11/1978 | Hassler | 367/94 |
| 4,346,717 | 8/1982 | Haerten | 128/660 |
| 4,355,643 | 10/1982 | Laughlin et al. | 128/663 |

Primary Examiner—Lee S. Cohen
Assistant Examiner—Angela D. Sykes
Attorney, Agent, or Firm—Moonray Kojima

[57] ABSTRACT

An ultrasonic probe for puncture treatments is constructed in a manner that a guide member, for guiding a puncture needle, is provided on a side surface of an ultrasonic probe of a linear scanning type, with a needle being positioned by the guide member to be movable at right angles to the surface of the body of a patient, and a beam of ultrasonic wave is emitted by the probe in a direction oblique to the length dimension of the needle. The probe may be positioned obliquely to the needle, in which case, an acoustic coupling member of a wedge shape is inserted in the gap formed between the emitting end of the probe and the body. Alternatively, the probe may be positioned parallel with the needle in which case a wedge shaped member capable of deflecting the ultrasonic waves, is placed on the emitting end of the probe, and a wedge shaped acoustic coupling member is connected to the deflecting member so as to deflect the ultrasonic waves to be oblique to the needle within the body. The needle may be an acupuncture needle, a cannula, a tube, or the like.

5 Claims, 7 Drawing Figures

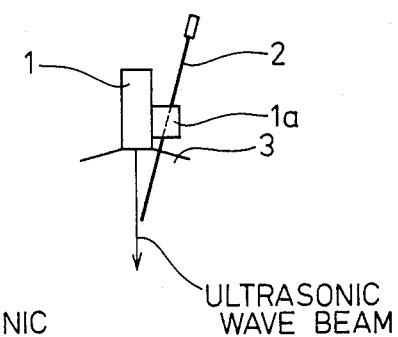
FIG. 1b (PRIOR ART)
FIG. 1a (PRIOR ART)
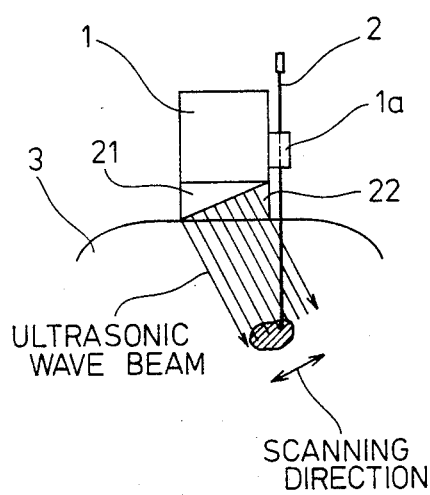
FIG. 2
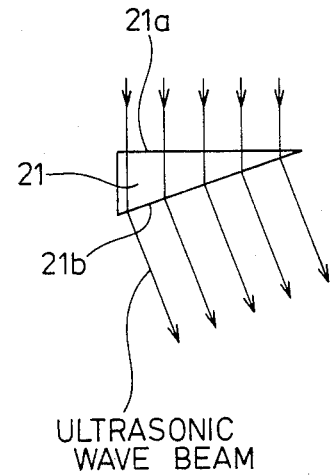
FIG. 3

ULTRASONIC PROBE FOR PUNCTURE TREATMENT

This is a continuation of application Ser. No. 344,361, filed Feb. 1, 1982, now abandoned.

BACKGROUND OF THE INVENTION

1. Field of the Invention

This invention relates to ultrasonic probes for placement of implements through the surface of a body to be diagnosed or treated, and more particularly to such a probe for accurately positioning said implement during such diagnosis or treatment while observing an objective organ or other part of a body being diagnosed or treated.

2. Description of the Prior Art

Heretofore, diagnosis and treatment involving placement of an implement through the skin of a patient, including accurate placement of needles used therein, have totally relied on the sense and judgment of the operator. However, recently, it has been made possible to carry out the same easily and accurately by attaching the needle or other implement, to an ultrasonic probe which enabled the visualization of the objective organ or other part of the patient.

Since the organ or other part to be diagnosed or treated, varies in a wide range, from those storing liquid substances (e.g. gall bladder) to those of a tubular construction (e.g. biliary duct), and also varied as to size from large to extremely small, the following points are required to be satisfied by an ultrasonic probe used for diagnosis or treatment involving puncture type operation using an implement such as a needle, in order to be capable of inspecting these organs or other parts, in their operating condition.

(1) The ultrasonic image is not lost at part of the puncture hole.

(2) Substantially the entire length of the needle is visible.

(3) The needle can reach the objective organ or part, following the shortest path between the surface and the organ or part.

(4) The probe should be positioned so that the part of the body surface to be punctured is freely observable.

However, disadvantageously, prior art arrangement of such ultrasonic probes were as typically shown in FIGS. 1(a) and 1(b), which depict a needle 2 introduced into the body of a patient from outside of an ultrasonic probe through a guide member 1a, attached to the probe, in a direction perpendicular to the scanning direction of the ultrasonic wave. This prior art arrangement has various disadvantages, such as an image of the entire needle cannot be obtained; the part of the surface of the patient's body to be punctured is not easily observable; and the guide member 1a is closely positioned to the body surface and should be thoroughly disinfected prior to use, but usually is not.

In another conventional construction wherein the ultrasonic beam is caused to be emitted obliquely to the needle by sector scanning of the same beam, it was found that luster became rough at a long distance.

In still another prior art arrangement, wherein the ultrasonic beam was emitted obliquely by driving the ultrasonic probe with time delays, it was apparent that complicated expensive circuits were necessary because of the delayed drive, and that the directivity of the beam deteriorated.

In another prior art arrangement, wherein the needle was introduced into the body from the outside of the probe in a direction parallel with the scanning direction of the ultrasonic beam, it was found that the introduction angle of the needle was excessive and the needle did not take the shortest path from the body surface to the organ or other part being diagnosed or treated.

SUMMARY OF THE INVENTION

An object of the invention is to provide an ultrasonic probe for puncture treatments, wherein all of the aforementioned disadvantages of prior art arrangements, are substantially eliminated or overcome, and wherein all of the above listed requirements (1) through (4) are satisfied.

Briefly, the invention comprises a guide member, a needle held by the guide member, and an ultrasonic probe connected to the guide member, wherein the positioning of the aforementioned components are such as to cause the needle to be driven perpendicularly to the surface of the patient's body being treated. Also, provided are a deflector member attached to the probe, and an acoustic coupling member which is held against the body and is of a material which is similar in sound velocity as the human body. The deflector member deflects the ultrasonic waves to be oblique to the direction of the needle. In one embodiment, the probe is positioned to be parallel with the needle, with the probe emitting ultrasonic waves which are parallel to the needle, and then are deflected by the deflector member. In another embodiment, the probe is positioned oblique to the needle, and the ultrasonic waves are generated to be directed oblique to the needle, either in the direction of scanning or perpendicular to the direction of scanning. In the latter embodiments, there is no need for a deflector member since the ultrasonic waves are directed by the probe in a direction oblique to the needle. In both these embodiments, an acoustic coupling is employed between the body surface and the emitting end of the probe. Advantageously, the invention enables accurate placement of acupuncture needles, needles, tubes, cannulas and the like in diagnosis of treatment operations.

BRIEF DESCRIPTION OF THE DRAWINGS

FIGS. 1(a) and 1(b) depict front and side elevational views of a prior art needle puncture treatment device employing an ultrasonic probe;

FIG. 2 depicts a side elevational view of an illustrative embodiment of the invention.

FIG. 3 depicts operation of the deflector member used in the embodiment of FIG. 2;

DETAILED DESCRIPTION OF THE PREFERRED EMBODIMENTS

Figure 4:
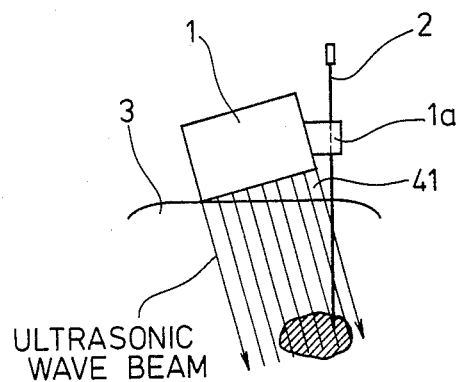
FIG. 4 depicts a side elevational view of another illustrative embodiment of the invention.

In FIG. 2, needle 2 is held by guide member 2, which is attached to ultrasonic probe 1, in the manner depicted, that is with the probe 1 being disposed to have the needle parallel to the direction of emission of ultrasonic waves. In this arrangement, advantageously, the positioning of the needle, guide member, and probe, enables the needle to be driven perpendicularly to the surface of body 3 of a patient being diagnosed and/or treated. A deflecting member 21 and an acoustic coupling member 22 are disposed at the end of the probe 1 which emits the ultrasonic waves. The deflector member 21 deflects the ultrasonic waves from a parallel direction to an oblique direction to the needle 2. As shown in FIG. 3, the deflecting member 21, being of a suitable material, and shape, causes the ultrasonic waves to be bent from the parallel direction to the oblique direction. Deflector member 21 has a cross sectional configuration of a right angled triangle with the base 21a connected to the emitting end of the probe 1. The probe 1 generates ultrasonic waves which are directed perpendicular to the surface 21a, and then the waves are transmitted through the member 21 in the same direction until they hit the surface 21b, at which point they are bent to travel in a direction which is oblique to the length dimension of the needle 2. The deflector member 21 may be made of any suitable material, such as acrylic resin, and the like, which perform the function just outlined.

The acoustic coupling member 22 (see FIG. 2) couples the deflecting member effectively to the body 3 of the patient, and is made of any suitable substance, such as water or castor oil, which has the property of governing velocity of sound passing therethrough which is nearly the same as that of the human body being treated and/or diagnosed (approximately 1.5 mm/$\mu$s), or other body being treated and/or diagnosed. The substance of the medium is preferably enclosed in a rubber film or vinyl chloride film or the like. In the depicted embodiment, the acoustic coupling member 22 is formed in a configuration which is symmetrical to the deflecting member 21, so that the probe 1 and needle 2, are thereby maintained vertical with respect to the surface 3 of the patient's body.

According to the above arrangement, needle 2 can be readily disposed to be perpendicular to the surface 3 of the body being diagnosed, examined or/and treated, thereby enabling the needle to reach the objective organ (shown, but not numbered), following the shortest path from the surface 3 to the organ or other part. Also, the ultrasonic waves can be guided obliquely to substantially the entire part of needle 2 capable of being driven into the patient's body, so that an image of substantially the entire part of the needle 2 can be obtained.

FIG. 4 depicts another illustrative embodiment of the invention, wherein the ultrasonic probe 1 is positioned obliquely to the scanning direction, while an acoustic coupling member 41, of a triangular shape, is inserted between the emitting end of probe 1, and the surface 3 of a patient's body. Needle 2 is positioned by guide member 1a to be vertical to the surface 3 of the body. With the above described arrangement, it is apparent that the ultrasonic waves from probe 1, are directed obliquely to substantially the entire part of needle 2 driven in the body. Thus, as depicted the plane of the scanning is substantially perpendicular to the oblique intersection of the ultrasonic waves with the lengthwise dimension of the needle.

Figure 5A:
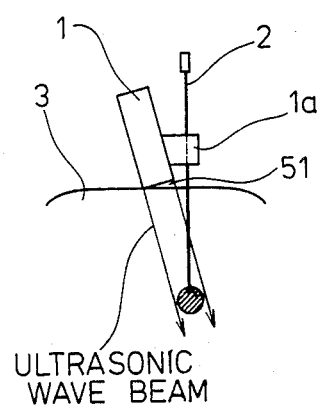
FIGS. 5(a) and 5(b) depict side and front elevational views of a further illustrative embodiment of the invention.
Figure 5B:
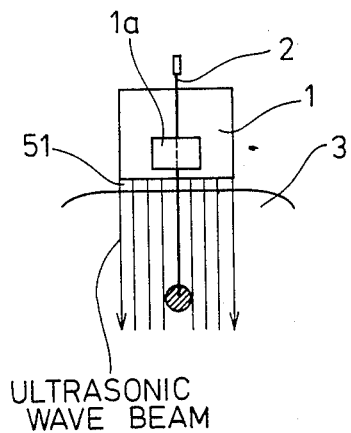

The positioning of the ultrasonic probe 1 is not necessarily limited to the above described direction shown in FIG. 4. In FIGS. 5a and 5b are depicted another positioning of the probe. In this embodiment, the probe is so positioned vis-a-vis the needle, that the plane of scanning is oblique to the lengthwise dimension of the needle, as depicted. In this embodiment of FIGS. 5a and 5b, acoustic coupling member 51, having a triangular cross section shape, is inserted between the probe and body surface so as to position probe 1 to be oblique to the thickness direction of probe 1, and the needle 2 is positioned perpendicularly to the surface of the patient's body. With this arrangement, it is also apparent that the ultrasonic waves can be directed obliquely to substantially the entire part of needle 2 entering into the body. Although the arrangement of FIG. 5 is less favorable than the construction of FIG. 4, in terms of stability and the portion of the needle which is visualized in the image, the FIG. 5 arrangement is more favorable from the viewpoint of the acoustic coupling member being of a smaller size.

The invention can be employed for many different uses. For example, the probe can be employed for accurate placement of various implements, and for more comprehensive image readout of the implement and surroundings, and of the puncture area and of the organ or part under observation. The needle can, for example, be an acupuncture needle, which may be used to accurately touch certain nerve endings. The needle can also be a hollow tube, or a cannula, for example, and be used to drain an objective organ or part. Also, various proble structures can be accurately fixed and placed by the probe, and the objective part or area or organ observed in the image created by the ultrasonic waves. Thus, the term needle as used herein, in intended to cover and encompass all such implements and uses. The term puncture is employed when the implement goes through the skin or surface of the body. But, also covered would be open areas which need not be punctured by the implement itself. For example an implement or needle may be inserted through a body opening. The term ultrasonic waves is well known in the art and encompasses those wavelengths of sound generally above the audible range, i.e. to the human ear.

As described above, according to the present invention, there is provided an ultrasonic probe for diagnosis and/or treatment involving placement of an implement, such as a needle, in a body, such as that of a human, and, for example, touching a particular part of the body, such as an organ. The inventive arrangement is disposed in a manner to enable the needle to be placed perpendicular to the surface of the body, with linear scanning with ultrasonic waves emitted from the probe, the waves being directed obliquely to and upon the entire length of the needle that is driven in the body, whereby substantially the entire interior part of the needle and the leading end of the needle are observable in the image without losing any part of the parts being scanned.

The foregoing description is illustrative of the principles of the invention. Numerous extensions and modifications thereof would be apparent to the worker skilled in the art. All such extensions and modifications are to be considered to be within the spirit and scope of the invention.

What is claimed is:

1. An ultrasonic diagnosis and/or treatment device comprising a needle, a guide member means for holding said needle; and a linear scanning probe means for generating ultrasonic waves; wherein said needle, said guide member means and said probe means are cooperatively arranged so that said needle can be driven perpendicularly to and into the surface of and into a patient's body, while concurrently a plurality of parallel ultrasonic waves emitted from said probe means are, in a linear scan, incident upon said needle, all at the same oblique angle within said patient's body and concurrently incident upon a desired part of said patient's body, whereby said needle is guided directly and accurately to said desired part of said patient's body.

2. The device of claim 1, wherein said probe means is positioned obliquely to said needle, and wherein said probe means comprises an acoustic coupling member having a cross-section of a triangular shape, and of a material which transmits said ultrasonic waves in a straight line without any substantial deflection to the surface of said body.

3. The device of claim 1, wherein said probe means comprises a deflecting member means having a triangular cross-section and of a material capable of suitably deflecting said ultrasonic waves, said deflecting member means being attached to an end of said probe means emitting said ultrasonic waves, an acoustic coupling member having a triangular cross-section disposed adjacent to said deflecting member means opposite said surface of said body, whereby said ultrasonic waves are transmitted through said deflecting member to be incident obliquely to said needle regardless of the position of said probe means and said needle means.

4. The device of claim 1, wherein said probe means is positioned to emit ultrasonic waves in a scanning direction obliquely to said needle, with the plane of the scanning being parallel to the needle means lengthwise dimension of the needle.

5. The device of claim 1, wherein said probe means is positioned to emit ultrasonic waves in a scanning direction obliquely to said needle, with the plane of scanning cutting the lengthwise dimension of said needle.

* * * * *